United States Patent
Presthus et al.

(10) Patent No.: US 6,685,623 B2
(45) Date of Patent: Feb. 3, 2004

(54) INCONTINENCE TREATMENT WITH URETHRAL GUIDE

(75) Inventors: James B. Presthus, Edina, MN (US); Timothy G. Dietz, Califon, NJ (US); Stanley Levy, Jr., Saratoga, CA (US); F. Allen House, Pleasanton, CA (US); Steven H. Trebotich, Newark, CA (US)

(73) Assignee: SURx, Inc., Livermore, CA (US)

( * ) Notice: Subject to any disclaimer, the term of this patent is extended or adjusted under 35 U.S.C. 154(b) by 2 days.

(21) Appl. No.: 09/991,368

(22) Filed: Nov. 20, 2001

(65) Prior Publication Data

US 2003/0097038 A1 May 22, 2003

(51) Int. Cl.⁷ .............................. A61F 2/00; A61N 1/30
(52) U.S. Cl. .......................................... 600/29; 604/19
(58) Field of Search .................. 600/29, 374, 461, 600/30–35; 601/46; 604/22, 19, 51, 54, 55, 164, 93, 27, 117, 264, 280; 606/144, 87, 91; 607/98, 105, 99, 102; 128/898, 885, DIG. 25

(56) References Cited

U.S. PATENT DOCUMENTS

| 4,742,829 A | * | 5/1988 | Law et al. .................. 600/461 |
| 4,838,506 A | | 6/1989 | Cooper |
| 4,846,818 A | | 7/1989 | Keldahl et al. |
| 4,946,443 A | | 8/1990 | Hauser et al. |
| 5,239,999 A | * | 8/1993 | Imran ......................... 600/374 |
| 5,304,214 A | * | 4/1994 | DeFord et al. .............. 607/105 |
| 5,433,720 A | * | 7/1995 | Faccioli et al. ............... 606/87 |
| 5,836,314 A | * | 11/1998 | Benderev et al. ........... 128/898 |
| 5,848,986 A | * | 12/1998 | Lundquist et al. ............ 604/22 |
| 5,995,875 A | * | 11/1999 | Blewett et al. ............... 607/98 |
| 6,071,230 A | * | 6/2000 | Henalla ....................... 600/29 |
| 6,081,749 A | | 6/2000 | Ingle et al. |
| 6,091,995 A | | 7/2000 | Ingle et al. |
| 6,136,010 A | * | 10/2000 | Modesitt et al. ............ 606/144 |
| 6,139,569 A | | 10/2000 | Ingle et al. |
| 6,159,170 A | * | 12/2000 | Borodulin et al. ............ 601/46 |
| 6,216,704 B1 | * | 4/2001 | Ingle et al. ................. 128/898 |
| 6,236,891 B1 | | 5/2001 | Ingle et al. |
| 6,283,987 B1 | | 9/2001 | Laird et al. |
| 6,292,700 B1 | | 9/2001 | Morrison et al. |
| 6,460,542 B1 | * | 10/2002 | James ......................... 128/885 |
| 6,480,746 B1 | * | 11/2002 | Ingle et al. .................. 607/99 |

* cited by examiner

Primary Examiner—Eric F. Winakur
Assistant Examiner—Nikita R Veniaminov
(74) Attorney, Agent, or Firm—Townsend and Townsend and Crew LLP

(57) ABSTRACT

Devices and methods for aligning a probe body and electrodes adjacent a target tissue. A guide shaft can be coupled to the probe body for entering a first body orifice. The probe body can be positioned in a second body orifice such that coupling of the probe body and guide shaft positions the electrodes adjacent the target tissue. In exemplary embodiments, the guide shaft is coupled at an offset angular alignment from the probe body.

44 Claims, 12 Drawing Sheets

INCONTINENCE TREATMENT WITH URETHRAL GUIDE

BACKGROUND OF THE INVENTION

The present invention relates generally to medical devices methods, systems, and kits. More specifically, the present invention provides devices and methods for positioning electrodes to selectively heat and shrink tissues, particularly for the noninvasive treatment of urinary incontinence, hernias, cosmetic surgery, and the like.

Urinary incontinence arises in both women and men with varying degrees of severity, and from different causes. In men, the condition occurs almost exclusively as a result of prostatectomies which result in mechanical damage to the sphincter. In women, the condition typically arises after pregnancy where musculoskeletal damage has occurred as a result of inelastic stretching of the structures which support the genitourinary tract. Specifically, pregnancy can result in inelastic stretching of the pelvic floor, the external vaginal sphincter, and most often, the tissue structures which support the bladder and bladder neck region. In each of these cases, urinary leakage typically occurs when a patient's intra-abdominal pressure increases as a result of stress, e.g. coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt behavior modification intended to reduce the incidence of urinary leakage.

In cases where such noninterventional approaches are inadequate or unacceptable, the patient may undergo surgery to correct the problem. A variety of procedures have been developed to correct urinary incontinence in women. Several of these procedures are specifically intended to support the bladder neck region. For example, sutures, straps, or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

It has recently been proposed to selectively deliver RF energy to gently heat fascia and other collagenated support tissues to treat incontinence. One problem associated with delivering RF energy to the targeted tissue is the alignment of the electrodes with the target tissue. Direct heating of target tissue is often complicated since the target tissue is offset laterally and separated from the urethra by triangular shaped fascia sheets supporting the urethra. These urethra-supporting fascia sheets often contain nerve bundles and other structures that would not benefit from heating. In fact, injury to these nerve bundles may even promote incontinence, instead of providing relief from incontinence.

For these reasons, it would be desirable to provide improved devices, methods, systems, and kits for providing improved alignment devices and methods that would improve the positioning of heating electrodes adjacent the target tissue and away from the surrounding, sensitive nerve bundles.

BRIEF SUMMARY OF THE INVENTION

The present invention provides devices, methods, systems, and kits for positioning a treatment surface, such as electrodes, adjacent a target tissue, particularly for treating urinary incontinence.

The probes and guides of the present invention can accurately position a treatment surface, such as an electrode array, adjacent a target tissue. The present invention utilizes the human anatomy to help guide the treatment surface into contact with the target tissue. Generally, the probe can be inserted in a first body orifice and the guide can be inserted in a second body orifice to guide and position the treatment surface adjacent the target tissue.

In exemplary embodiments, the guide can be inserted into the urethra to help position the treatment surface adjacent the target tissue in the vagina. As illustrated in FIG. 8, the urethra U is supported by triangular shaped fascia sheets FS is that have nerve bundles. Delivery of electrical energy into the fascia sheets FS is undesirable. The electrical energy is preferably delivered to the endopelvic fascia EF that is spaced laterally to both sides of the urethra. To offset the probe body away from the fascia sheets and urethra, a longitudinal axis of the guide can be aligned in an angled arrangement with a longitudinal axis of the probe body. The angled offset moves the probe body laterally (left or right) away from the urethral tissue and fascia sheets and adjacent the target endopelvic fascia EF for treatment.

The probes of the present invention generally includes a probe body comprising a treatment surface. A urethral guide can be coupled to the probe body in an offset alignment relative to the probe body. The urethral guide is positionable in the urethra so as to align the treatment surface with a target tissue, and away from non-target tissue.

Optionally, the urethral guide will be removably attached to the probe body. The removable attachment allows the probe body and urethral guide to be independently inserted into the body. After both have been inserted, the two can be attached to align the treatment assembly with the target tissue. Optionally, the probes of the present invention may have a coupling structure on each side of the probe body to provide proper alignment of the treatment surface with target tissue both to the left and right of the urethra.

Exemplary guides of the present invention can also be configured to bias the electrodes into the target tissue. Such biasing can improve the efficiency of electrical energy delivery and can reduce the amount of current that arcs to the surrounding non-target tissue, if the electrodes are not in proper contact with the target tissue.

Unlike conventional intrauterine catheters, both the probe body and guide means will typically be rigid and rigidly connected to each other. The rigid configuration of the probes of the present invention allows the physician to maintain the position of the treatment surface relative to the target tissue.

The guides of the present invention can also optionally include an expansible member adjacent its distal end. The urethral guide can be moved through the urethra and into the patient's bladder. Once in the bladder, the expansible member can be expanded so as to prevent proximal movement of the urethral guide and probe body.

The methods of the present invention generally comprise guiding a treatment surface, such as an electrode to a target tissue with an offset guide. Once the treatment surface is positioned against the target tissue, the target tissue can be treated. Typically, treatments comprise delivering an electrical energy to heat and shrink or stiffen the target tissue.

One method of the present invention comprises inserting a treatment probe having a treatment surface, such as an electrode array, into a first body orifice (e.g., vagina). A guide is placed into a second body orifice (e.g., urethra). The probe can be coupled to the guide either before insertion of the guide and probe body into the body orifices, or after insertion of the guide and probe body into the body orifices, to position the treatment surface in the proper alignment with a target tissue in the vagina. In order to accurately position the electrode array away from the non-target urethra, the treatment probe can have a guide that offsets the treatment surface laterally away from the urethral tissue. Typically the angle of offset between the probe and the shaft will be between approximately 5° degrees and 30° degrees, and preferably approximately 15° degrees.

The present invention further provides kits for treating incontinence. The kits of the present invention typically include any of the probes and guides as described above. The kits will generally include a package for holding the probe, guide, and instructions for use which describe any of the exemplary methods described herein. Optionally, the kits may include a controller, power source, electrical connections, or the like.

A further understanding of the nature and advantages of the invention will become apparent by reference to the remaining portions of the specification and drawings.

DESCRIPTION OF THE SPECIFIC EMBODIMENTS

The present invention provides methods, devices, systems, and kits for accurately positioning a treatment assembly, such as an electrode array, adjacent fascia and other collagenated tissues to selectively treat the target tissue. In a particular embodiment, the present invention accurately directs an electrical current flux through the target tissue between bipolar electrodes that are contacting the target tissue to shrink or stiffen the collagenated tissue.

Exemplary embodiments of the present invention treat target tissue in the vagina for treating urinary incontinence. The urethra is composed of muscle structures that allow it to function as a sphincter controlling the release of urine from the bladder. These muscles are controlled by nerve bundles that, in part, run in close proximity to the urethra-bladder junction and along the axis of the urethra. Pelvic surgery in this region has been associated with the development of intrinsic sphincter deficiency of the urethra. It is therefore important that any tissue treatment avoid areas containing nerve pathways that supply the urethra. Because the present invention provides accurate placement with the target tissue, collateral damage to surrounding nerve bundles and other organs can be reduced.

While the remaining discussion will be directed at treating incontinence in a female patient, it should be appreciated that the concepts of the present invention are further applicable to other noninvasive and invasive surgical procedures.

Figure 1A:
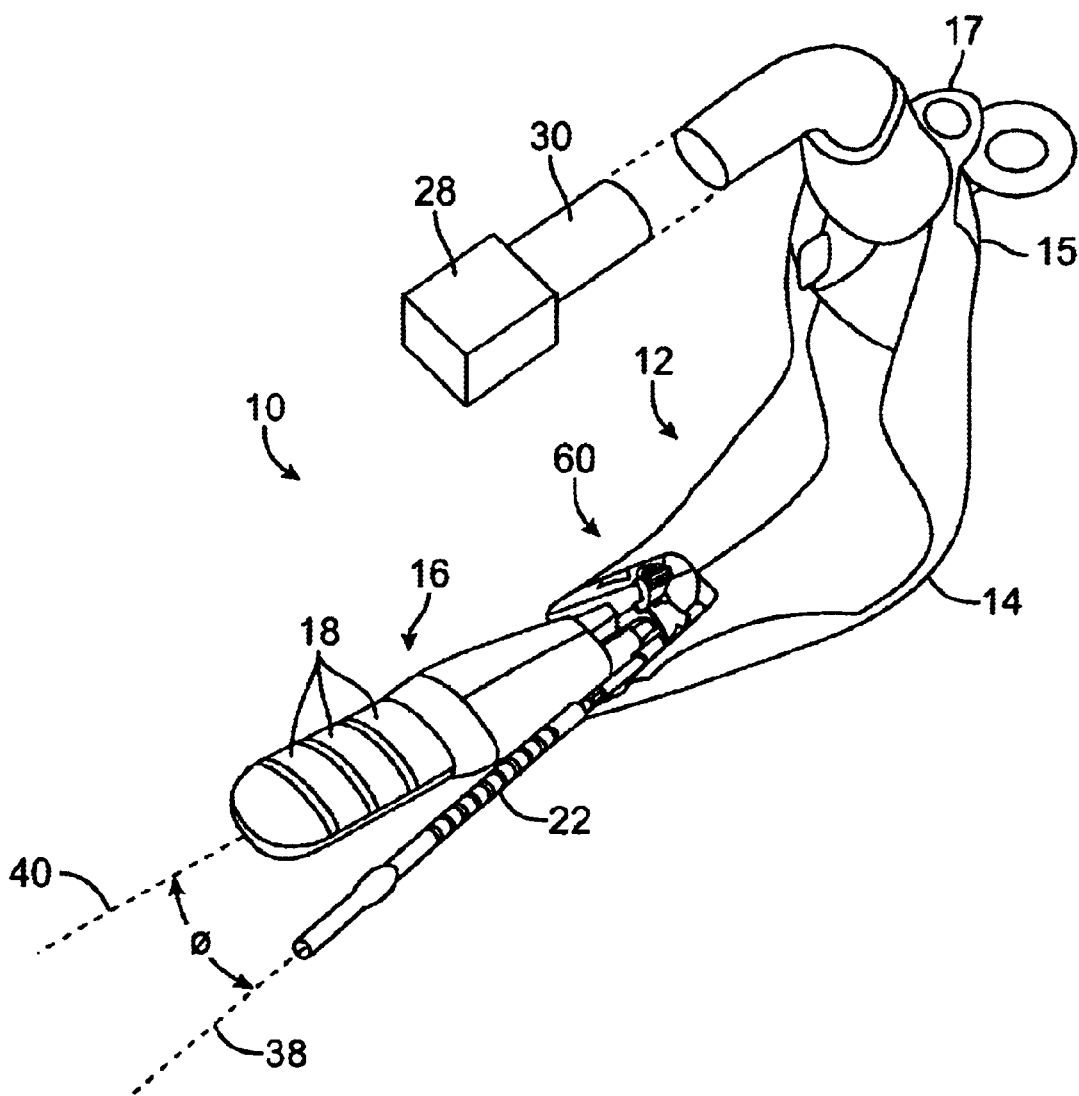
FIG. 1A illustrates an exemplary electrosurgical probe of the present invention.

FIG. 1A illustrates an exemplary electrosurgical probe 10 of the present invention. The electrosurgical probe includes an applicator or probe body 12 having a proximal portion 14 and a distal portion 16. Proximal portion 14 of the probe body 12 generally includes a handle 15 and a trigger or switch 17 for activating a delivery of electrical energy to the target tissue or for deploying a temperature probe into the target tissue to monitor the tissue temperature during treatment. Distal portion 16 includes a treatment surface 18 that has at least one electrode or other type of treatment assembly, such as an electrode on a needle, ultrasound transducer, microwave antenna, or needle for delivery of a therapeutic agent (not shown). A guide body or shaft 22 can be attached to the probe body 12 to assist in the proper positioning of the distal portion 16 of probe body 12 and treatment surface 18 with a target tissue.

Systems of the present invention further include a power supply 28 that is in electrical communication with the electrode assembly 18 through electrical couplings 30. Optionally, a controller (not shown) may be incorporated into the probe or the power supply to control the delivery of energy to the heating electrodes. Some exemplary controllers are described in commonly assigned U.S. Pat. No. 6,081,749, the complete disclosure of which is incorporated herein by reference.

Exemplary probes of the present invention are for use in treating incontinence. Such probes will be substantially rigid, and sized and shaped to be insertable into a patient's vagina. In such embodiments, the distal portion will have a length between approximately 4 cm and 8 cm, and will have a width or diameter between approximately 1.5 cm and 3.0 cm. The probes can be composed of a plastic (such as polyester polycarbonate, or the like) or an inert metal (such as gold plated brass, or the like), or other bio-compatible materials that are typical of intravaginal devices.

The electrodes 18 of the present invention can take a variety of forms. As illustrated in FIG. 1A, the heating electrodes can include a plurality of curved electrodes disposed on the distal portion 16 of probe body 12. In the illustrated embodiment, there are three curved electrodes 18. It should be appreciated however, that any number of electrodes and a variety of shaped electrodes can be used. A more complete description of various types of electrodes that can be used with the devices and methods of the present invention are shown and described in commonly assigned U.S. Pat. No. 6,091,995, the complete disclosure of which is incorporated herein by reference.

Figure 2:
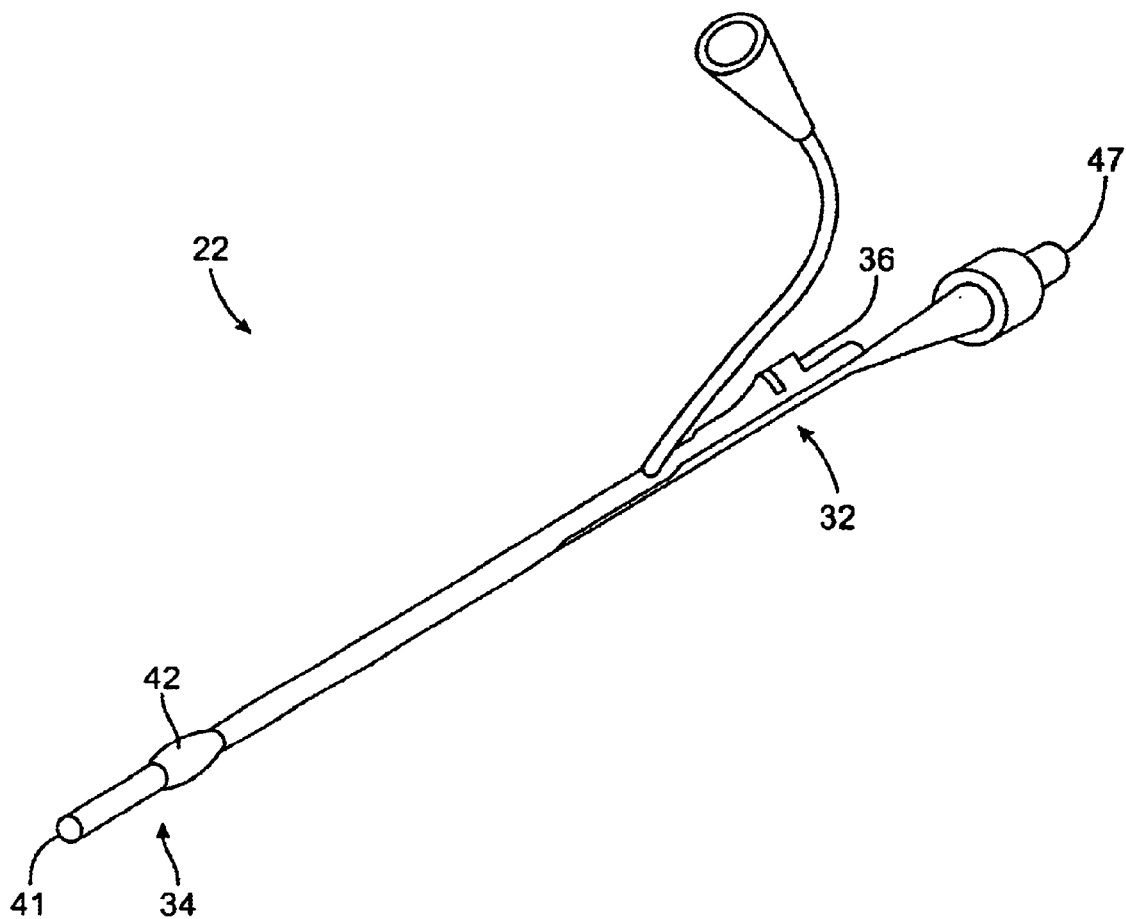
FIG. 2 illustrates a urethral guide shaft of the present invention.

FIG. 2 illustrates an exemplary embodiment of the guide shaft 22 of the present invention. The guide shaft 22 has a proximal portion 32 and a distal portion 34. In exemplary embodiments, guide shaft 22 of the present invention is removably attached to the probe body 12 to allow for independent placement of the probe 10 and guide shaft 22 in the patient's body. A clamping structure 36, such as serrations, is disposed on the proximal portion 32 to allow the guide 22 to be removably attached to the probe body 12.

Figure 3:
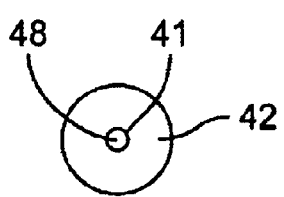
FIG. 3 is a simplified end view of a distal orifice and expansible member disposed on guide shaft.
Figure 4:
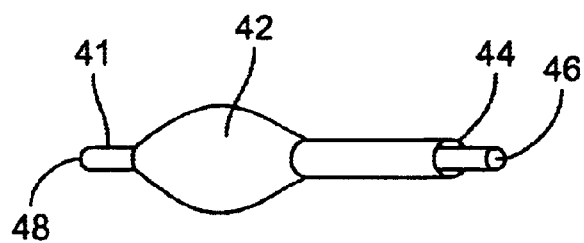
FIG. 4 is a simplified side view of the expansible member.

As illustrated in FIGS. 2–4, guide 22 can optionally include a tip 41 and an expansible member 42 positioned on the distal portion 34 of guide 22. Expansible member 42 can be inflated and deflated via an inflation lumen 44. Guide 22 can also include a fluid lumen 46 that has a proximal orifice 47 and distal orifice 48. In the particular configuration illustrated in FIGS. 3 and 4, the fluid lumen 46 can be disposed through expansible member 42. The fluid lumen 46 can be used to deliver fluids to a body organ or to drain fluid from the body organ. Proximal orifice 47 of the fluid lumen 46 can be coupled to an aspiration or fluid source (not shown) to assist in the transfer of fluid through the fluid lumen 46. In such embodiments, expansible member 42 can be annular shaped and will have a corresponding annular inflation lumen 44 and fluid lumen 46 will be concentric or lateral with each other. It should be appreciated however, that a variety of other configurations of the lumens 44, 46 can be used without departing from the concepts of the present invention.

Guide 22 can be rigidly coupled to probe body 12 with a coupling assembly 60 so as to maintain a rigid assembly. By maintaining a substantially rigid connection, rigid guide 22 can properly position electrodes 18 offset laterally from a sensitive non-target tissue, such as the urethra, so that delivery of electrical energy through the electrodes 18 is sufficiently spaced from the non-target tissue.

Figure 8:
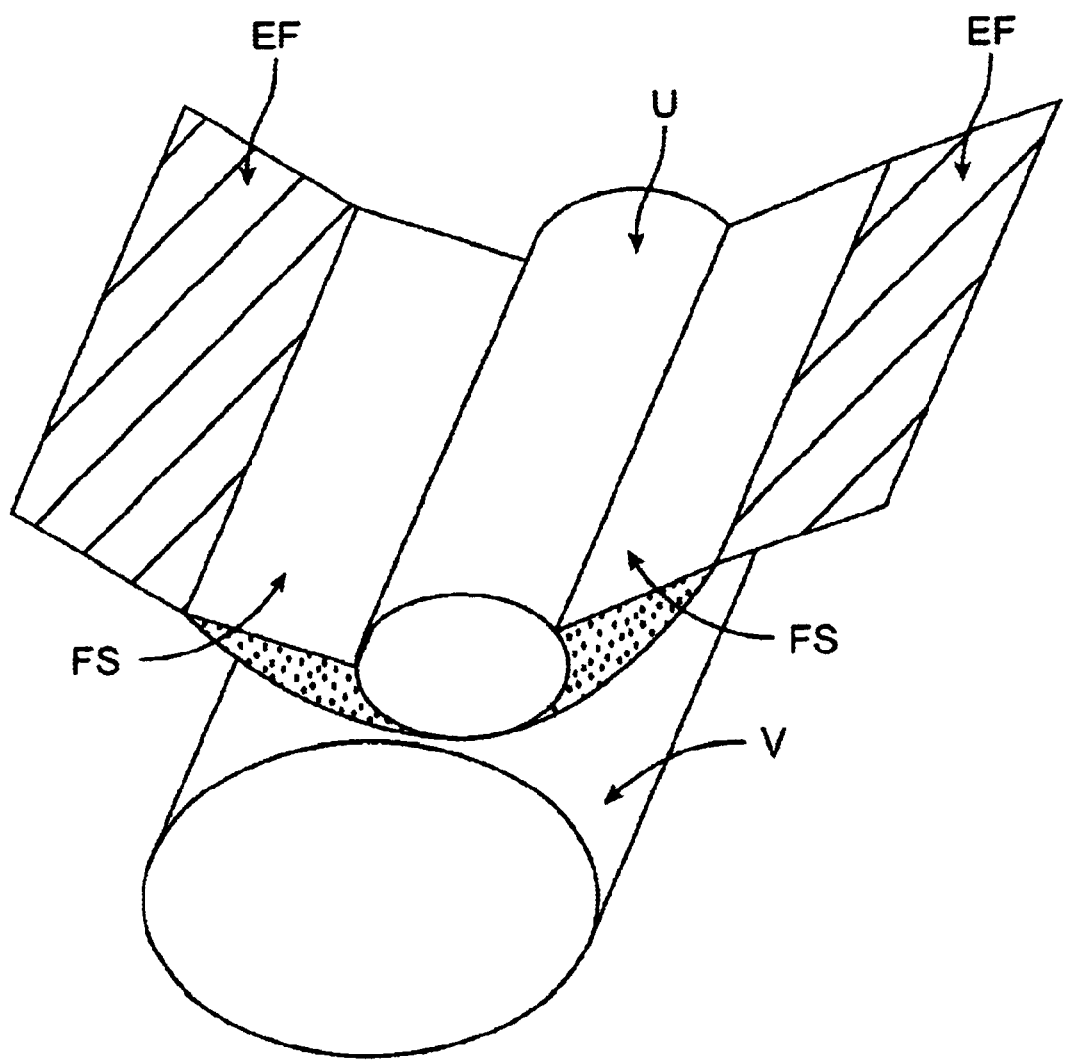
FIG. 8 is a simplified cross sectional front view of target tissue of an exemplary method of the present invention.
Figure 9:
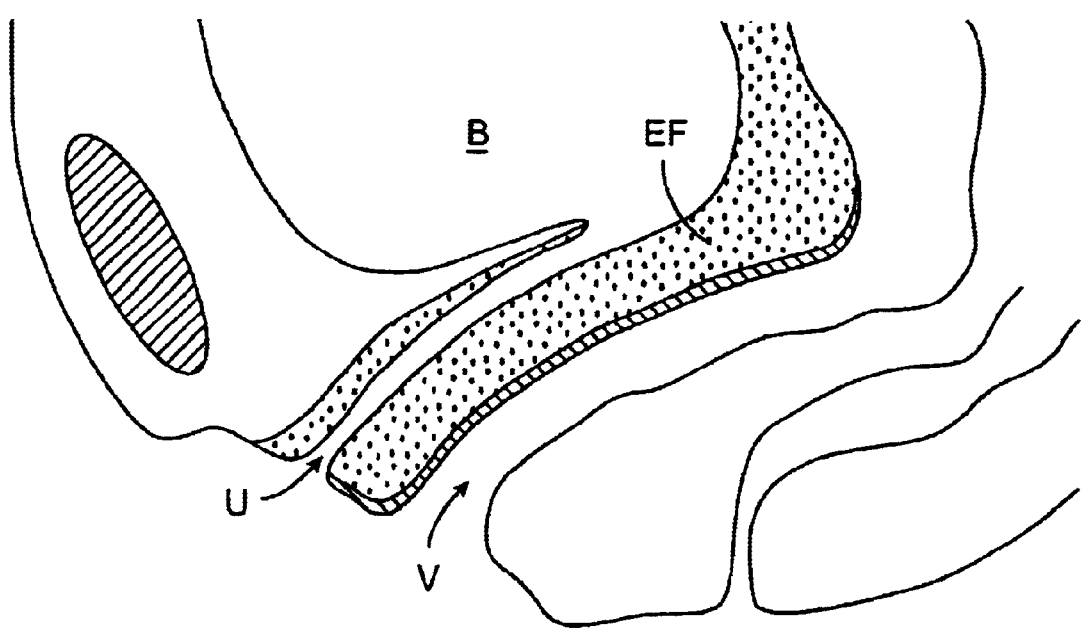
FIG. 9 is a sagittal view of the tissue that can be targeted for non-invasive treatment using the methods of the present invention.

In exemplary methods of the present invention, probe body 12 will be configured to be insertable in a first body orifice, while guide shaft 22 will be configured to be inserted into a second body orifice so as to accurately position the probe body 12 and electrodes 18 adjacent a target tissue in the first body orifice. Preferably, the probe body 12 will be positioned in an offset position relative to the guide 22. In a particular method, the guide shaft 22 is configured for insertion into a patient's urethra U while the probe body 12 will be configured for insertion into a patient's vagina V (FIGS. 8 and 9). In such embodiments, urethral guide 22 will generally have a diameter and length that allows a distal end 34 of the urethral guide 22 to extend through the patient's urethra U and into the patient's bladder B. As such, the urethral guide will have a length between approximately 5 inches and 6 inches and a diameter between approximately 0.12 inches and 0.24 inches.

In exemplary embodiments, a distal end of urethral guide 22 will also be positionable distal of the distal end 16 of the probe body. Thus, when the expansible member 42 of the guide extends into the bladder B, the electrodes 18 on the probe body 12 will be maintained in a position proximal of the bladder B. Such a configuration can prevent inadvertent delivery of electrical energy to the non-target bladder tissue.

Figure 5:
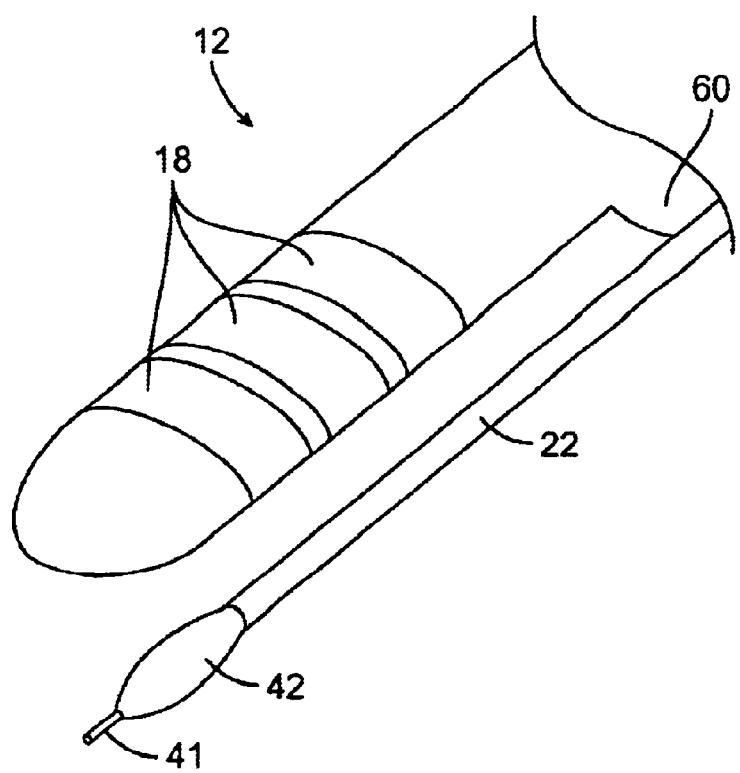
FIG. 5 is a simplified view of an alternative embodiment of the noninvasive probe of the present invention.
Figure 6:
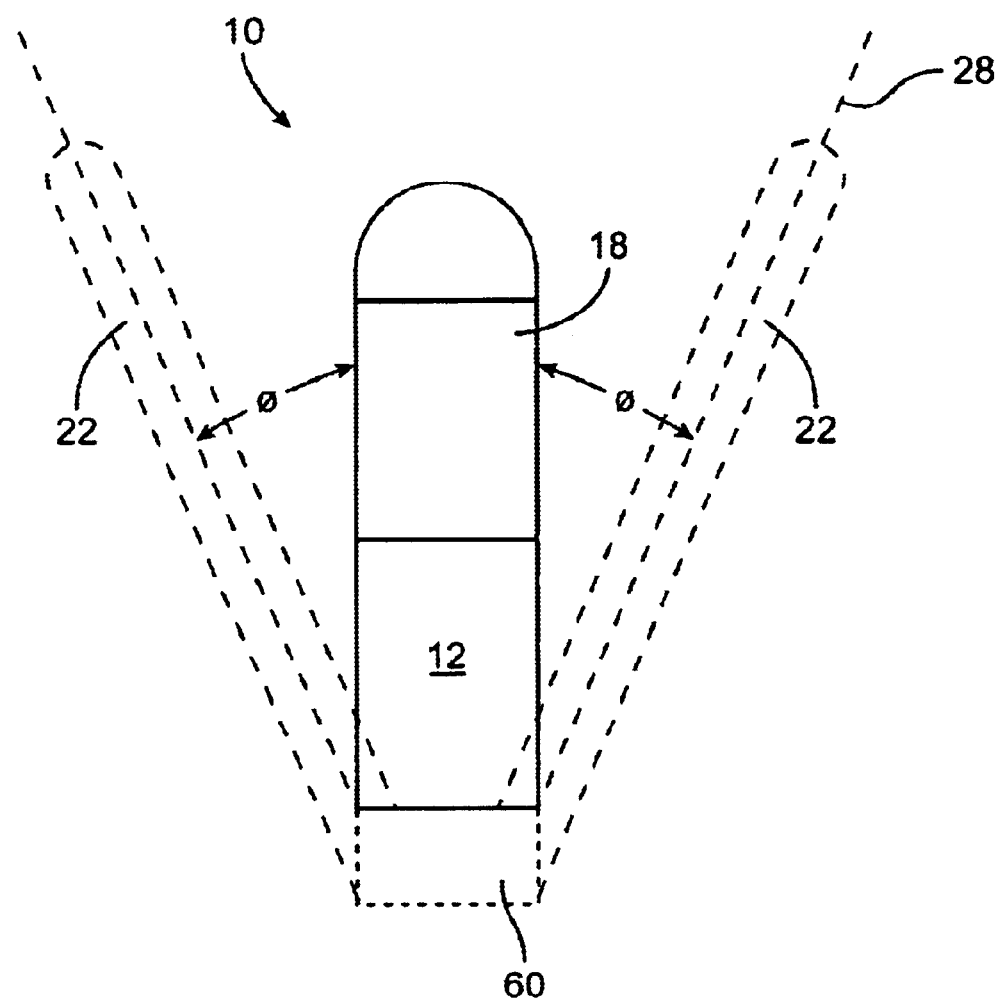
FIG. 6 illustrates an exemplary embodiment of a coupling structure on two sides of the probe body which allows for positioning of the probe body against target tissue on both the left and right side of the urethra.

Urethral guide 22 can also be coupled to the probe body 12 in an offset configuration (FIG. 1A). Typically, a longitudinal axis 38 of urethral guide 22 will be angled from a longitudinal axis 40 of the probe body 12 (FIGS. 1 and 6). The angle θ will typically be between approximately 5° degrees and 30° degrees, and preferably approximately 15° degrees. It should be appreciated, however, that in alternative embodiments, urethral guide 22 and probe body 12 may be in a parallel configuration (FIG. 5). The angled arrangement is more preferred than the parallel arrangement, because in the angled offset arrangement, as the probe is moved distally through the body orifice, the probe and guide will diverge along the angled path so that the electrodes will be positioned offset from the position of the guide and farther away from the urethra-bladder junction, which extends laterally from a longitudinal axis of the urethra.

Because of the offset configuration between guide 22 and probe 12, the electrodes 18 will be offset from urethra U and moved against the target tissue that is laterally spaced from the urethra (FIG. 8). In order to provide accurate positioning, urethral guide 22 should be substantially rigid so as to maintain its relative position between the electrode 18 and guide shaft 22. As such, guide 22 is also typically in the form of a rigid shaft. In exemplary embodiments, rigid guide 22 is at least partially composed of or covered with a biocompatible material that is typical of intraurethral catheter devices. If the guide shaft is too flexible, then the position of the electrodes 18 relative to the guide shaft 22 may not be maintained in the desired position and electrical energy may be inadvertently delivered to non-targeted tissue (e.g. urethra and and/or nerve bundles surrounding urethra).

In some configurations, the coupling assembly 60 of the present invention can be configured to allow attachment to the probe body along both sides of the probe body. As shown in FIG. 6, urethral guide 22 can be positioned laterally along either the left or right side so as to allow contact of the electrodes 18 with tissue laterally to the left or right of the urethra.

Figure 1B:
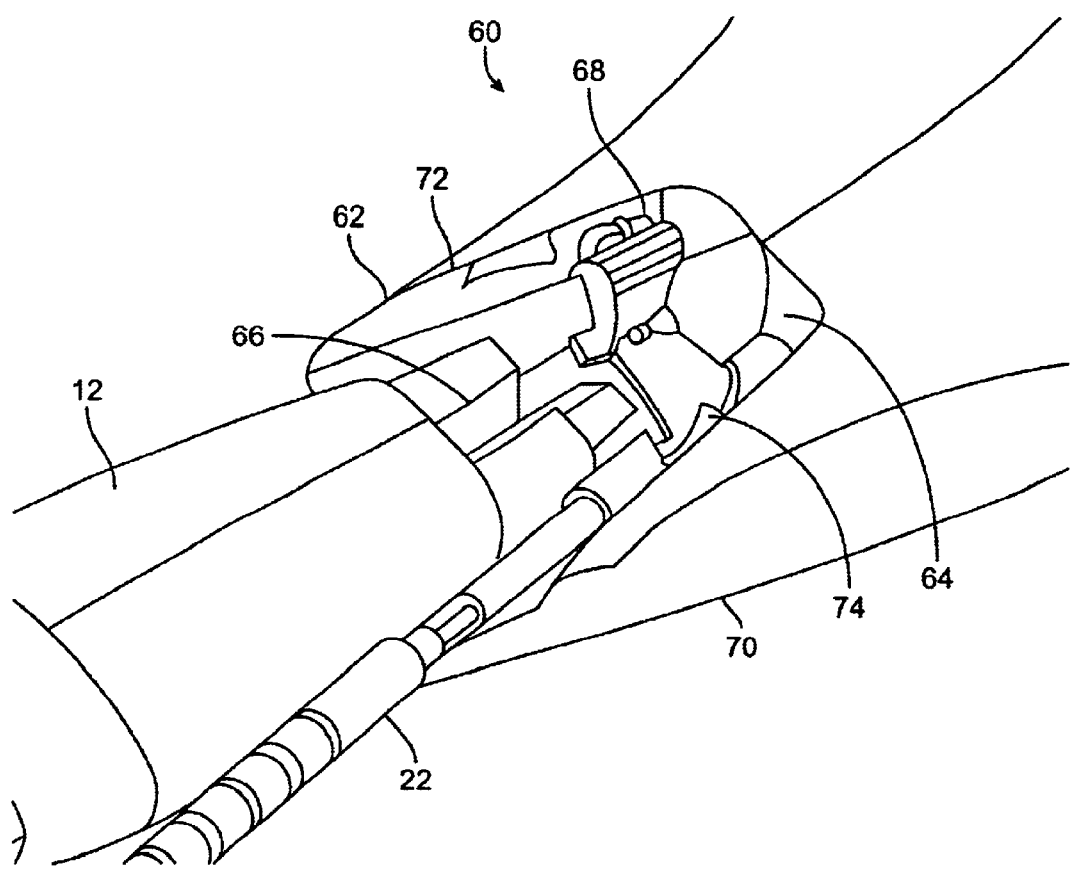
FIG. 1B is a close up perspective view of an exemplary coupling assembly.

The coupling assembly 60 of the present invention can provides an attachment between the guide 22 and the probe body 12 that allows the user to attach and detach the guide to position the electrodes adjacent the target tissue. One exemplary coupling assembly is illustrated in FIG. 1B. The coupling assembly includes a substantially symmetrical left and right pockets 62, 64 that can receive a proximal end of the urethral guide 22. A rotatable guide clip 66 having a left and right coupling handles 68, 70 is disposed between left pocket 62 and right pocket 64. The left pocket 62 and right pocket 64 can include a serrated mount 72 that can interact with clamping structure 36 on the proximal end of the guide 22. Additionally, the pockets 62, 64 can include a snap feature 74 that can interact with the left and right coupling handles to lock the guide within the pockets.

In use, the urethral guide can enter the pockets either by vertically or axially sliding the proximal end of the urethral guide 22 into a selected pocket. In exemplary embodiments, the proximal end of the urethral guide 22 includes matching serrations (not shown) that match the serrated mount 72 in the pocket so as to allow for incremental axial positioning of the urethral guide with respect to the applicator and handle. After the guide 22 is positioned in a desired axial position, the selected handle 68, 70 can be secured by snapping it into the snap feature 74.

It should be appreciated however, that other conventional attachment means can be used to attach the urethral guide 22 to the probe body 12. For example, the guide 22 and probe body 12 can be coupled with a threaded attachment, a toggle clamp mechanism for pressing a clamping surface of the guide against the probe body, a sliding latch mechanism clip, a ¼ turn fastener, or the like.

Figure 7:
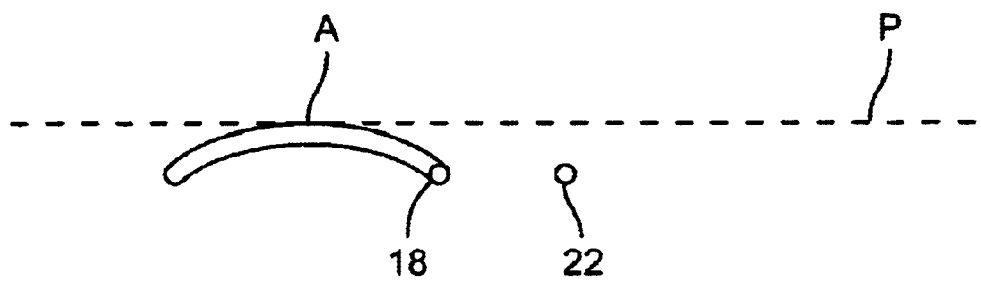
FIG. 7 is a simplified cross sectional view of a radiused electrode and a guide of the present invention illustrating a lateral offset of the guide relative to the probe body and an orthogonal offset relative to a plane of the electrode.

One exemplary configuration of the probe 10 is illustrated in FIG. 7. In such a configuration, the probe 10 includes radiused electrodes that have an apex A. The guide 22 will be offset laterally from an axis of the probe body 12, typically between 5° degrees to 30° degrees, and offset below a plane P that is orthogonal to the apex A (or parallel to an upper plane of a planar electrode). By offsetting the distal end of the guide 22 below the top plane of the electrode, the guide 22 can tension the vaginal surface tissue engaged by the probe body 12 and bias the electrodes 18 into contact with the target tissue. Such a biasing configuration can improve the delivery of the electrical energy from the electrodes 18 into the target tissue and reduce the chance of delivering energy to non-target tissue.

The devices and systems of the present invention can be used in a variety of invasive and noninvasive methods to treat tissue in a patient. Specifically, the present invention can be used to accurately position the treatment surface against target tissue to treat the endopelvic fascia EF as a treatment for incontinence. As illustrated in FIGS. 8 and 9, the urethra U is supported by triangular shaped fascia sheets FS that have nerve bundles. Delivery of electrical energy into the fascia sheets FS is undesirable. The electrical energy is preferably delivered to the endopelvic fascia EF that is spaced laterally to both sides of the urethra.

Figure 10:
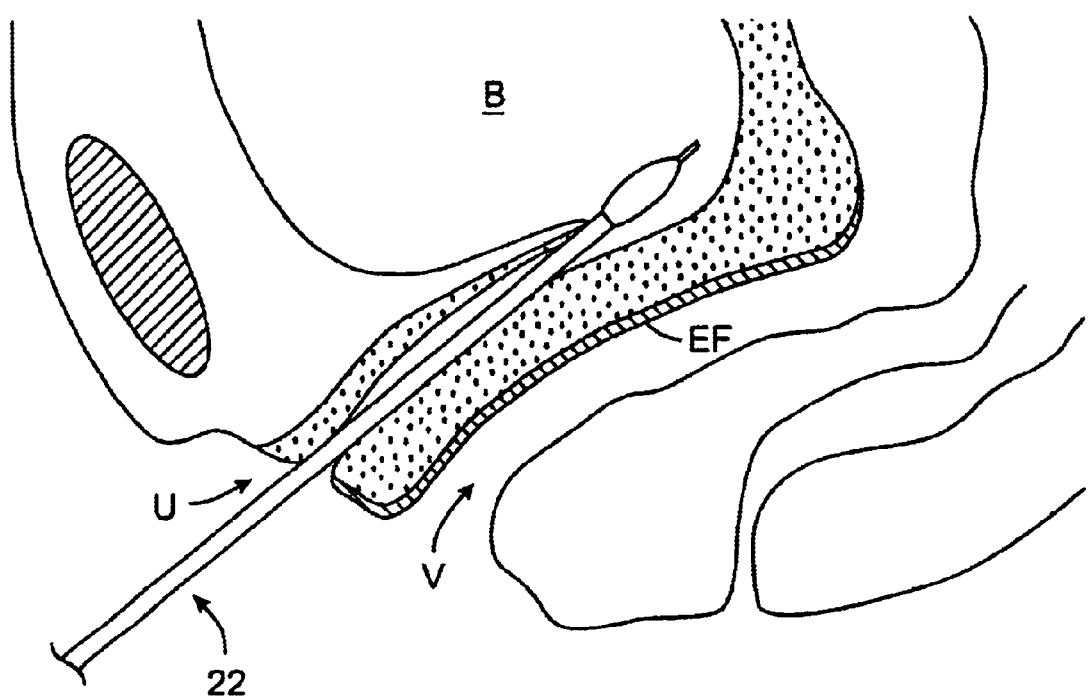
FIG. 10 illustrates placement of the guide into the urethra.
Figure 11:
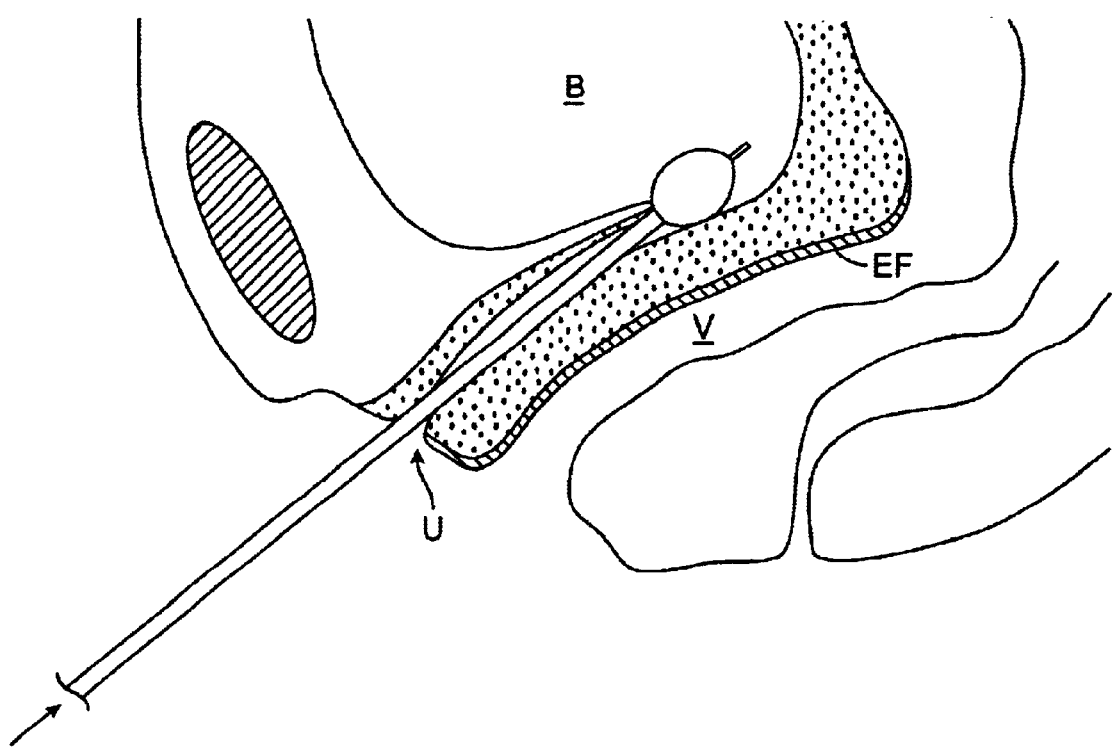
FIG. 11 illustrates expanding of the expansible member in the bladder.

An exemplary method is illustrated in FIGS. 10–13. In a noninvasive medical procedure to treat incontinence, the urethral guide 22 can be inserted into the urethra U (FIG. 10). During its distal movement through the urethra U, expansible member 42 will be in its deflated configuration. Once the expansible member enters the orifice to the bladder B, expansible member 42 can be inflated to "lock" the position of the urethral guide 22 to prevent proximal retraction of the urethral guide 22 out of the bladder B (FIG. 11). In some embodiments, the guide can include markings to ensure that the guide remains in the most proximal position allowed by the expansible member relative to the bladder orifice. Any liquid that is present in the bladder B can be drained out of the bladder B through the distal orifice 48 and fluid channel 46 within the urethral guide.

Figure 12:
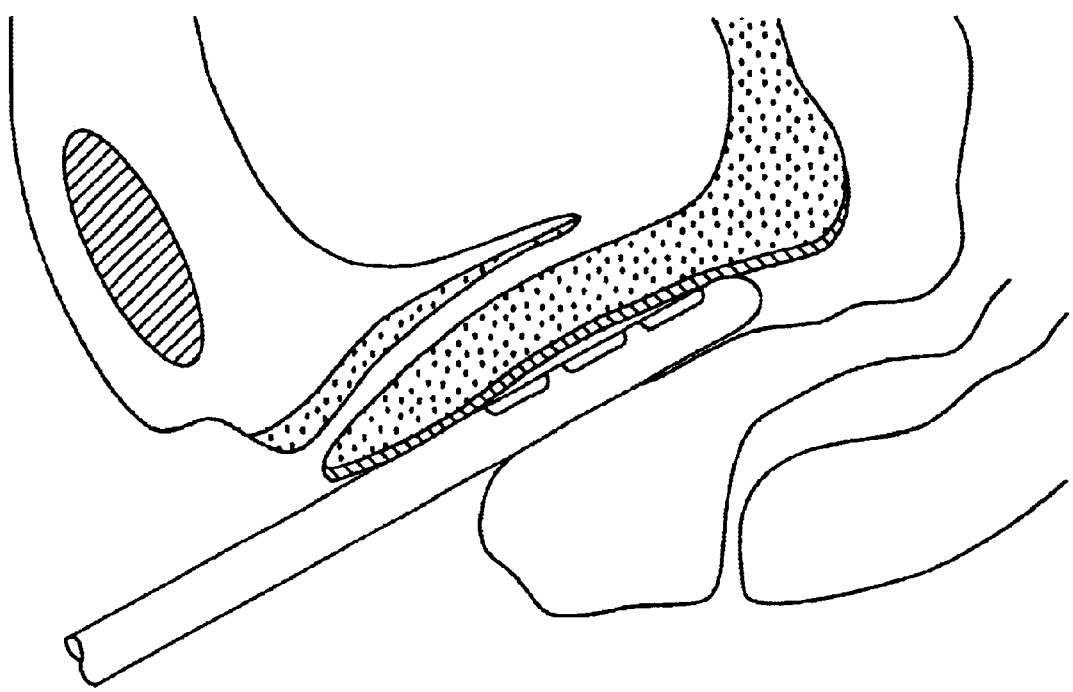
FIG. 12 illustrates placement of the probe into the vagina.
Figure 13:
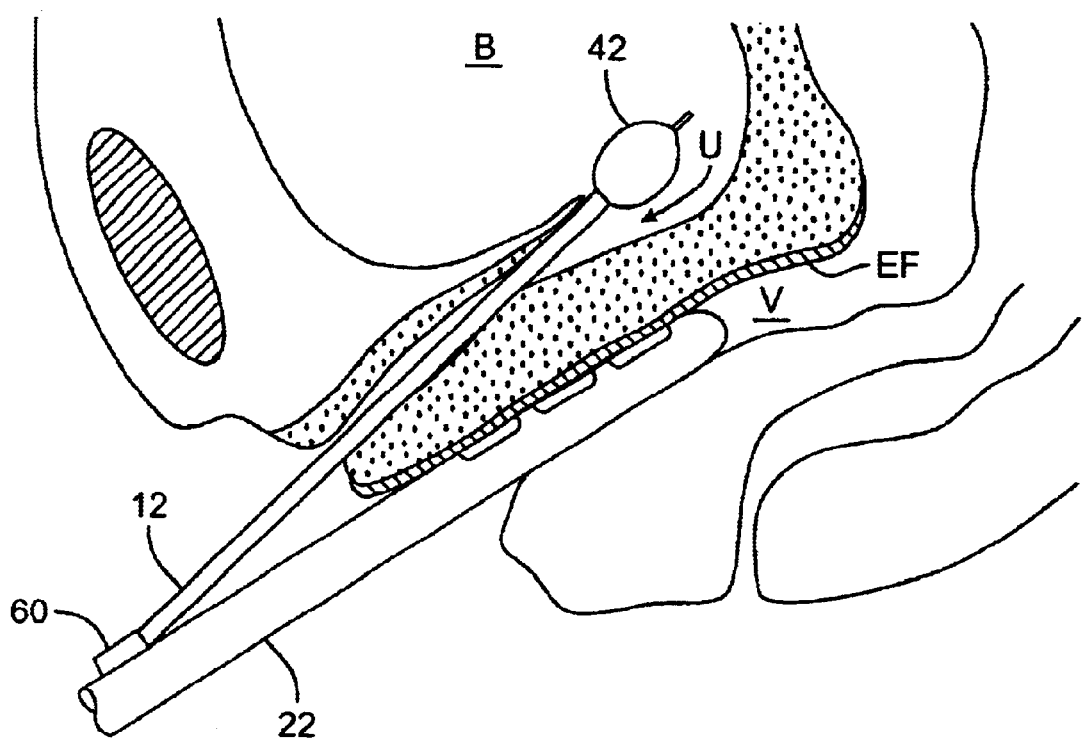
FIG. 13 illustrates coupling of the guide to the probe body in an offset configuration and treating the target tissue.

FIG. 12 illustrates that the probe body 12 can be inserted into the patient's vagina V. Once it is grossly determined that the probe has been inserted to the proper location the urethral guide and probe body can be attached together with the coupling structure 60 (FIG. 13). Such coupling will ensure that the distal tip of the probe body 12 is maintained proximal of the distal end of the guide 22 so as to position the treatment surface adjacent the target endopelvic fascia EF and to prevent the electrodes from delivering electrical energy to the bladder or other non-target tissue. The coupling structure also will maintain the offset configuration between the axes of the guide 22 and probe body 12 so as to position the electrodes offset laterally away from the urethra and towards the target tissue EF. Optionally, if the guide 22 is positioned below a top plane of the electrode, the guide may tension the tissue and bias the electrodes 18 into the target tissue EF.

While FIGS. 10 and 12 illustrate the urethral guide 22 and probe body 12 being separately inserted into the body orifices, it should be appreciated that the urethral guide 22 and probe body 12 can also be simultaneously inserted into the urethra U and vagina V while connected with coupling structure 60.

Figure 14:
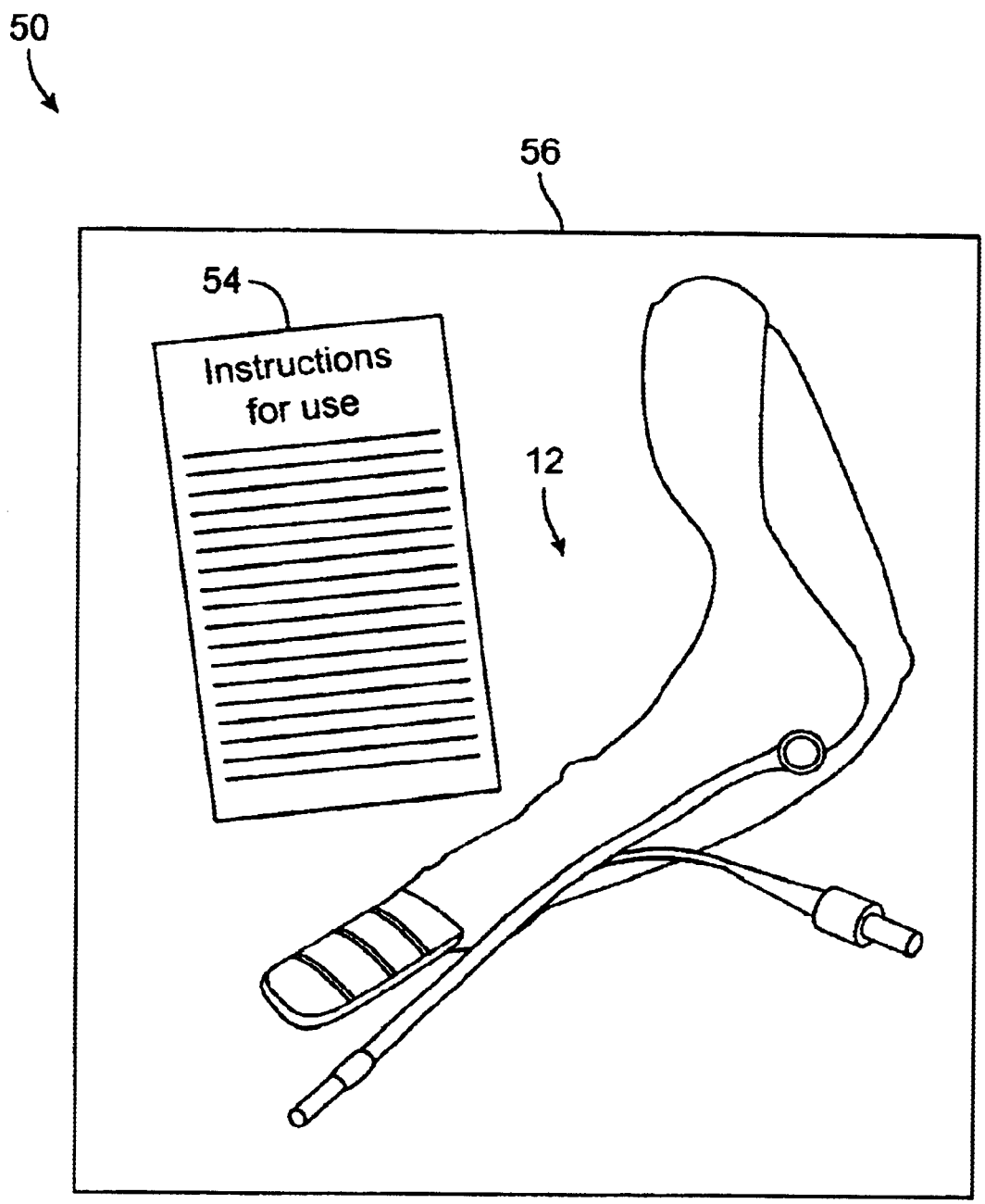
FIG. 14 illustrates a kit of the present invention.

Referring now to FIG. 14, a kit 50 includes a probe 12 and instructions for use 54. Probe 12 and instructions 54 can be placed in packaging 56. Instructions 54 will often set forth the steps of one or more of the methods described herein for heating and shrinking or stiffening tissue for treating urinary incontinence. Additional elements of the above described systems may also be included in packaging 56, or may alternatively be packaged separately.

Instructions 54 will often comprise printed material, and may also be found in whole or in part on packaging 56. Alternatively, instructions may be in the form of a recording disk, CD-ROM or other computer-readable medium, video tape, sound recording, or the like.

While the above is a complete description of the preferred embodiments of the inventions, various alternatives, modifications, and equivalents may be used. For example, it may be possible to make the angular offset of the urethral guide adjustable, laterally from the probe body and/or orthogonal to a plane of the electrode. Although the foregoing has been described in detail for purposes of clarity of understanding, it will be obvious that certain modifications may be practiced within the scope of the appended claim.

What is claimed is:

1. A vaginal probe comprising:
   a vaginal probe body comprising a treatment surface; and
   a urethral guide coupled to the vaginal probe body in an angled offset alignment relative to the vaginal probe body, wherein the urethral guide is positionable in the urethra to align the treatment surface with a target tissue.

2. The vaginal probe of claim 1 wherein the urethral guide is removably attachable to the probe body.

3. The vaginal probe of claim 2 further comprising a clamping structure for attaching the urethral guide to the probe body.

4. The vaginal probe of claim 1 wherein the probe body defines a longitudinal axis and the urethral guide defines a longitudinal axis, wherein the longitudinal axis of the probe body and the longitudinal axis of the urethral guide are in a nonparallel alignment.

5. The vaginal probe of claim 4 wherein the longitudinal axis of the urethral guide is angled between approximately 5 degrees and 30 degrees from the longitudinal axis of the probe body.

6. The vaginal probe of claim 1 wherein the treatment surface comprises at least one electrode.

7. The vaginal probe of claim 1 wherein the urethral guide comprises an expansible distal end.

8. The vaginal probe of claim 7 wherein the urethral guide comprises an inflation lumen coupled to the expansible distal end.

9. The vaginal probe of claim 7 wherein the expansible distal end in an expanded configuration positioned in the bladder locks the treatment surface in position.

10. The vaginal probe of claim 1 wherein the urethral guide comprises a fluid lumen for draining fluid from a patient's bladder.

11. The vaginal probe of claim 1 wherein the treatment surface defines a plane, wherein the urethral guide is positioned below the plane, wherein insertion of the urethral guide into the urethra biases the treatment surface against the target tissue.

12. The vaginal probe of claim 1 wherein the urethral guide is rigid.

13. The vaginal probe of claim 1 wherein the urethral guide and probe body are coupled in a rigid configuration.

14. The vaginal probe of claim 1 wherein a distal end of the urethral guide extends distally beyond a distal end of the probe body.

15. An electrosurgical probe for treating incontinence, the probe comprising:

an applicator comprising a proximal portion, a distal portion, and a longitudinal axis;

at least one electrode disposed on the distal portion of the body; and a guide coupled to the distal portion of the applicator, wherein the guide comprises a proximal portion, a distal portion, and a longitudinal axis;

wherein the longitudinal axis of the guide is angled from the longitudinal axis of the applicator.

16. The probe of claim 15 wherein the electrode defines a top plane, wherein the distal portion of the guide is positioned below the top plane.

17. The probe of claim 15 wherein the distal portion of the guide extends distally beyond the distal portion of the applicator.

18. The probe of claim 15 wherein the applicator and guide are rigid.

19. The probe of claim 15 wherein the guide comprises at least one lumen.

20. The probe of claim 19 wherein the lumen is in communication with an expansible member disposed at the distal portion of the guide.

21. The probe of claim 19 wherein the lumen comprises a distal opening.

22. An electrosurgical probe for treating incontinence, the probe comprising:

a vaginal probe body comprising a distal portion and a proximal portion;

a plurality of electrodes disposed on the distal portion of the probe body; and a urethral guide adapted to be positioned in the urethra while the vaginal probe body is positioned in the vagina;

wherein the urethral guide is attachable to the vaginal probe body at an offset angle, wherein the vaginal probe body and urethral guide are disposed in a rigid configuration so as to maintain the offset orientation of the electrodes relative to a target tissue when the urethral guide is positioned in the urethra.

23. The probe of claim 22 wherein a distal end of the urethral guide extends beyond the distal portion of the probe body.

24. A method for treating incontinence, the method comprising:

inserting a probe comprising a treatment surface into a first body orifice;

placing a guide into a second body orifice;

coupling the probe to the guide at an angled offset; and treating the target tissue with the treatment surface.

25. The method of claim 24 wherein inserting and placing are carried out independently.

26. The method of claim 24 wherein coupling is carried out after the inserting and placing.

27. The method of claim 24 wherein inserting and placing are carried out simultaneously.

28. The method of claim 27 wherein coupling is carried out prior to inserting and placing.

29. The method of claim 24 wherein a longitudinal axis of the guide and a longitudinal axis of the probe are between an angle of approximately 5 degrees and 30 degrees.

30. The method of claim 29 wherein coupling comprises attaching the guide in an offset alignment with the probe to align the treatment surface with a target tissue.

31. The method of claim 29 wherein locking comprises inflating an expansible member on the guide.

32. The method of claim 24 further comprising locking the guide in the second body orifice.

33. The method of claim 24 further comprising draining fluid from the second body orifice.

34. The method of claim 24 wherein treating comprises heating the target tissue.

35. The method of claim 24 further comprising biasing the treatment surface against the target tissue.

36. The method of claim 24 further comprising tensioning tissue adjacent the guide.

37. The method of claim 24 further comprising restraining the distal position of the probe.

38. The method of claim 24 wherein the first body orifice is a vagina and the second body orifice is a urethra.

39. The method of claim 38 wherein coupling comprises laterally offsetting the probe from urethral tissue towards an endopelvic fascia tissue.

40. A kit comprising:

a probe body comprising a treatment surface;

a guide attachable to the probe body;

instructions for use comprising inserting the guide into a first body orifice, inserting the probe body into a second body orifice, and coupling the guide to the probe body at an angled offset to align the treatment surface with a target tissue, and treating the target tissue with the treatment surface; and a package to hold the probe body and guide.

41. The kit of claim 40 wherein the treatment surfaces comprises at least one electrode.

42. The kit of claim 41 further comprising a power source that is attachable to the at least one electrode.

43. The kit of claim 42 further comprising an attachment structure for attaching the guide to the probe.

44. The kit of claim 43 wherein the clamping structure maintains an offset configuration between the guide and probe.

* * * * *